US012673059B2

(12) United States Patent
Lebioda et al.

(10) Patent No.: US 12,673,059 B2
(45) Date of Patent: Jul. 7, 2026

(54) METHODS FOR IMPROVING RENAL FUNCTION WITH A COMBINATION OF A BET BROMODOMAIN INHIBITOR AND A SODIUM DEPENDENT GLUCOSE TRANSPORT 2 INHIBITOR

(71) Applicant: Resverlogix Corp., Calgary (CA)

(72) Inventors: Kenneth Eugene Lebioda, Calgary (CA); Christopher Ross Armstrong Halliday, Calgary (CA); Aziz Naeem Khan, Calgary (CA)

(73) Assignee: Resverlogix Corp., Calgary (CA)

( * ) Notice: Subject to any disclaimer, the term of this patent is extended or adjusted under 35 U.S.C. 154(b) by 377 days.

(21) Appl. No.: 18/032,450

(22) PCT Filed: Oct. 29, 2021

(86) PCT No.: PCT/IB2021/060043
§ 371 (c)(1),
(2) Date: Apr. 18, 2023

(87) PCT Pub. No.: WO2022/091028
PCT Pub. Date: May 5, 2022

(65) Prior Publication Data
US 2023/0381178 A1 Nov. 30, 2023

Related U.S. Application Data

(60) Provisional application No. 63/107,853, filed on Oct. 30, 2020.

(51) Int. Cl.
*A61K 31/517* (2006.01)
*A61K 31/35* (2006.01)
*A61K 31/351* (2006.01)
*A61K 31/381* (2006.01)
*A61K 31/382* (2006.01)
*A61K 31/7034* (2006.01)
*A61P 13/12* (2006.01)

(52) U.S. Cl.
CPC ............ *A61K 31/517* (2013.01); *A61K 31/35* (2013.01); *A61K 31/351* (2013.01); *A61K 31/381* (2013.01); *A61K 31/382* (2013.01); *A61K 31/7034* (2013.01); *A61P 13/12* (2018.01)

(58) Field of Classification Search
CPC .............................. A61K 31/517; A61P 13/12
See application file for complete search history.

(56) References Cited

U.S. PATENT DOCUMENTS

| | | |
|---|---|---|
| 8,053,440 B2 | 11/2011 | Hansen |
| 8,410,109 B2 | 4/2013 | Wong et al. |
| 8,889,698 B2 | 11/2014 | Hansen |
| 9,199,990 B2 | 12/2015 | Hansen |
| 9,238,640 B2 | 1/2016 | Hansen |
| 9,610,251 B2 | 4/2017 | Shenoy |
| 9,757,368 B2 | 9/2017 | Hansen |
| 9,765,039 B2 | 9/2017 | Fairfax et al. |
| 10,111,885 B2 | 10/2018 | Kulikowski et al. |
| 10,131,640 B2 | 11/2018 | Hansen |
| 10,532,054 B2 | 1/2020 | Hansen |
| 10,752,595 B2 | 8/2020 | Chen et al. |
| 10,772,894 B2 | 9/2020 | Kulikowski et al. |
| 10,882,828 B2 | 1/2021 | Hansen |
| 11,407,719 B2 | 8/2022 | Hansen |
| 11,419,883 B2 | 8/2022 | Bhushan |

(Continued)

FOREIGN PATENT DOCUMENTS

| | | |
|---|---|---|
| WO | WO 2007/016525 A2 | 2/2007 |
| WO | WO 2008/092231 A1 | 8/2008 |

(Continued)

OTHER PUBLICATIONS

Kulikowski, E., et al., "Apabetalone Mediated Epigenetic Modulation is Associated with Favorable Kidney Function and Alkaline Phosphatase Profile in Patients with Chronic Kidney Disease," *Kidney & Blood Pressure Research* (2018), 43:449-457, DOI: 10.1159/000488257, published online: Mar. 22, 2018, Accepted: Mar. 13, 2018, © 2018 The Author(s), published by S. Karger AG, Basel, 9 pgs.

(Continued)

*Primary Examiner* — James D. Anderson
(74) *Attorney, Agent, or Firm* — Finnegan, Henderson, Farabow, Garrett & Dunner, LLP

(57) ABSTRACT

Described herein are methods for treating and/or preventing a kidney disease or an associated disorder as measured by an increase in estimated glomerular filtration rate (eGFR) by administering to a subject in need thereof, a combination of a sodium-glucose transport protein 2 (SGLT2) inhibitor and a compound of Formula I or a stereoisomer, tautomer, pharmaceutically acceptable salt, or hydrate thereof, wherein the variables of Formula I are as defined herein.

Formula I

17 Claims, 3 Drawing Sheets

(56)                    References Cited

U.S. PATENT DOCUMENTS

| | | | |
|---|---|---|---|
| 2016/0106750 | A1 | 4/2016 | Hansen |
| 2016/0206617 | A1 | 7/2016 | Lebioda et al. |
| 2016/0346291 | A1 | 12/2016 | Lebioda |
| 2017/0326143 | A1 | 11/2017 | Hansen et al. |
| 2017/0333419 | A1 | 11/2017 | Hansen et al. |
| 2020/0129512 | A1 | 4/2020 | Hansen et al. |
| 2020/0352946 | A1 | 11/2020 | Hansen |
| 2021/0361656 | A1 | 11/2021 | Hansen |
| 2022/0370452 | A1 | 11/2022 | Lebioda et al. |
| 2023/0241064 | A1 | 8/2023 | Lebioda et al. |

FOREIGN PATENT DOCUMENTS

| | | | |
|---|---|---|---|
| WO | WO 2009/158404 | A2 | 12/2009 |
| WO | WO 2010/138535 | A1 | 12/2010 |
| WO | WO 2013/186612 | A1 | 12/2013 |
| WO | WO 2014/170383 | A1 | 10/2014 |
| WO | WO 2015/025226 | A2 | 2/2015 |
| WO | WO 2015/025228 | A2 | 2/2015 |
| WO | WO 2016/147053 | A1 | 9/2016 |
| WO | WO 2018/225041 | A1 | 12/2018 |
| WO | WO 2021/090061 | A1 | 5/2021 |
| WO | WO 2021/140418 | A1 | 7/2021 |
| WO | WO 2022/091028 | A1 | 5/2022 |
| WO | WO 2022/091029 | A1 | 5/2022 |

OTHER PUBLICATIONS

The CANTATA-M (CANagliflozin Treatment and Trial Analysis—Monotherapy) Trial. ClinicalTrials.gov identifier: NCT01081834. Updated Feb. 23, 2017. Accessed Dec. 5, 2024. https://clinicaltrials.gov/study/NCT01081834—study results.

CANVAS—CANagliflozin cardioVascular Assessment Study (CANVAS). ClinicalTrials.gov identifier: NCT01032629. Updated Dec. 7, 2018. Accessed Dec. 5, 2024. https://clinicaltrials.gov/study/NCT01032629—study plan documentation.

Neal, B. et al., "Rationale, design and baseline characteristics of the CANagliflozin cardioVascular Assessment Study-Renal (CANVAS-R): A randomized, placebo-controlled trial," *Diabetes Obes. Metab.* 2017, 19(3), 387-393.

A Safety and Efficacy Study of Canagliflozin in Older Patients (55 to 80 Years of Age) With Type 2 Diabetes Mellitus. ClinicalTrials.gov identifier: NCT01106651. Updated Nov. 4, 2014. Accessed Dec. 5, 2024. https://clinicaltrials.gov/study/NCT01106651—Study Results.

Yale, J-F. et al., "Efficacy and safety of canagliflozin in subjects with type 2 diabetes and chronic kidney disease," *Diabetes Obes. Metab.* 2013, 15(5), 463-473.

Yamout, H. et al., "Efficacy and safety of canagliflozin in patients with type 2 diabetes and stage 3 nephropathy," *Am. J. Nephrol.* 2014, 40(1), 64-74.

Perkovic, V., et al. (2015) Renal effects of canagliflozin in type 2 diabetes mellitus. Current Medical Research and Opinion, 31(12), 2219-2231.

Ruiz-Ortega, M., et al., "Targeting the progression of chronic kidney disease," Nature Reviews. Nephrology, vol. 16, No. 5, Feb. 14, 2020, pp. 269-288, DOI: 10.1038/S41581-019-0248-Y.

Anker, S. D. et al., "Empagliflozin in Heart Failure with a Preserved Ejection Fraction," N. Engl. J. Med. 2021, 385(16), 1451-1461. doi: 10.1056/NEJMoa2107038.

Anonymous: "Apabetalone fails to benefit MACE, but 'cautious optimism' remains", cardiology today, Nov. 18, 2019 (Nov. 18, 2019), pp. 1-2, XP093115888, Retrieved from the Internet: URL: https://www.healio.com/news/cardiology/20191118/apabetalone-fails-to-benefit-mace-but-cautious-optimismremains [retrieved on Jan. 4, 2024].

Cannon, C. P. et al. (2020) Cardiovascular Outcomes with Ertugliflozin in Type 2 Diabetes. N. Engl J Med, 383, 1425-1435. DOI: 10.1056/NEJMoa2004967.

Giugliano, D. et al., "Heart failure and type 2 diabetes: From cardiovascular outcome trials, with hope," Diabetes Obes Metab. 2019, 21, 1081-1087. DOI: 10.1111/dom.13629.

Kluger et al. "Class effects of SGLT2 inhibitors on cardiorenal outcomes," Cardiovasc Diabetol (2019) 18:99, 14 pages. https://doi.org/10.1186/s12933-019-0903-4.

Kluger et al. "Cardiorenal Outcomes in the CANVAS, DECLARE-TIMI 58, and EMPA-REG OUTCOME Trials: A Systematic Review," Rev. Cardiovasc. Med. 2018; 19(2): 41-49. DOI:10.31083/j.rcm.2018.02.907.

Kosiborod, M. et al., "Lower Risk of Heart Failure and Death in Patients Initiated on Sodium-Glucose Cotransporter-2 Inhibitors Versus Other Glucose-Lowering Drugs," Circulation (2017) 136, 249-259. DOI: 10.1161/CIRCULATIONAHA.117.029190.

Kosiborod, M. et al., "Cardiovascular Events Associated With SGLT-2 Inhibitors Versus Other Glucose-Lowering Drugs," JACC (2018) 23(17), 2628-2639. https://doi.org/10.1016/j.jacc.2018.03.009.

Kulikowski, E. et al., (Jun. 2016). RVX-208 Affects Epigenetics to Lower Major Adverse Cardiovascular Events (MACE) in Atherosclerotic Patients and Especially in Ones with Diabetes Mellitus. In Diabetes (vol. 65, pp. A317-A317).

Lajthia, E. et al. Combination therapy with once-weekly glucagon like peptide-1 receptor agonists and dipeptidy1 peptidase-4 inhibitors in type 2 diabetes: a case series. Pharmacy Practice. (2019). 17(4): 1588. 6 pages.

Lim, J. et al., "Comparison of cardiovascular and renal outcomes between dapagliflozin and empagliflozin in patients with type 2 diabetes without prior cardiovascular or renal disease," PLOS One (2022) 17(0): e0269414. 14 pages. https://doi.org/10.1371/journal.pone.0269414.

McMurray, J.J.V. et al., "Dapagliflozin in Patients with Heart Failure and Reduced Ejection Fraction," N. Engl. J. Med. (2019) 381:1995-2008. DOI: 10.1056/NEJMoa1911303.

Nicholls, S. J., et al., "Apabetalone and hospitalization for heart failure in patients following an acute coronary syndrome: a prespecified analysis of the BETonMACE study," Cardiovasc. Diabetol. (2021) 20:13, 9 pages. https://doi.org/10.1186/s12933-020-01199-x.

Ray K K et al: "P4608BET-inhibition with Apabetalone in Post-ACS Patients with Diabetes: Design and Baseline Characteristics of the BETonMACE trial", European Heart Journal, vol. 40, No. Supplement_ 1, Oct. 1, 2019 (Oct. 1, 2019), XP093115548, gb Issn: 0195-668X, DOI: 10.1093/eurheartj/ ehz745.0991 Retrieved from the Internet: URL:http://academic.oup.com/eurheartj/article-pdf/40/Supplement_1/ehz745.0991/30201372/ehz745.0991.pdf.

Ray Kausik K et al: "Effect of BET Protein Inhibition With Apabetalone on Cardiovascular Outcomes in Patients With Acute Coronary Syndrome and Diabetes—Results of the BETonMACE Trial", Nov. 16, 2019 (Nov. 16, 2019), pp. 1-22, XP093115559 [retrieved on Jan. 3, 2024].

Sundström, J. et al. Synergistic effects of blood pressure-lowering drugs and statins: systematic review and meta-analysis. BMJ Evid Based Med. (2018). 23(2): 64-69.

Taeger, T. et al., "Comparative efficacy of sodium-glucose cotransporter-2 inhibitors(SGLT2i) for cardiovascular outcomes in type 2 diabetes: a systematic review and network meta-analysis of randomised controlled trials" Heart Failure Reviews (2021) 26:1421-1435. https://doi.org/10.1007/s10741-020-09954-8.

Yael Maxwell L: "Apabetalone Falls Short in Diabetic ACS Patients With Low HDL: BETonMACE," Nov. 21, 2019 (Nov. 21, 2019), pp. 1-12, XP093116050, Retrieved from the Internet: URL:https://www.tctmd.com/news/apabetalone-falls-short-diabetic-acs-patients-low-hdlbetonmace [retrieved on Jan. 4, 2024].

Clegg, Lindsay E. et al., "Reduction of Cardiovascular Risk and Improved Estimated Glomerular Filtration Rate by SGLT2 Inhibitors, Including Dapagliflozin, Is Consistent Across the Class: An Analysis of the Placebo Arm of EXSCEL," Diabetes Care, vol. 42, Feb. 2019, https://doi.org/10.2337/dc18-1871, © 2018 by the American Diabetes Association, care.diabetesjournals.org, 9 pgs.

Ghosh, G.C. et al., "RVX 208: A Novel BET Protein Inhibitor, Role as an Inducer of APO A-1/HDL and Beyond," Wiley Cardiovascular Therapeutics, https://doi.org/10.1111/1755-5922.12265, © 2017 John

(56) References Cited

OTHER PUBLICATIONS

Wiley & Sons Ltd., wileyonlinelibrary.com/journal/cdr, revised: Dec. 17, 2016, Accepted: Apr. 13, 2017, 10 pgs.

Gilham, D. et al., "Apabetalone Downregulates Fibrotic, Inflammatory and Calcific Processes in Renal Mesangial Cells and Patients with Renal Impairment," Biomedicines 2023, 11(6), 1663; https://doi.org/10.3390/biomedicines11061663.

Gilham, D. et al., "#2999 Apabetalone Reduces Cardiac Events in CKD Patients by Downregulating Fibrotic and Inflammatory Processes," Nephrology Dialysis Transplantation, vol. 38, Issue Supplement_1, Jun. 2023, gfad063c_2999, https://doi.org/10.1093/ndt/gfad063c_2999.

Guettier, J.M., "Endocrinologic and Metabolic Drugs Advisory Committee (EMDAC) Meeting, Jun. 28, 2016." U.S. Food and Drug Administration (FDA). 135 pgs.

Madaan, T. et al., "Sodium glucose Co Transporter 2 (SGLT 2) inhibitors: Current status and future perspective". European Journal of Pharmaceutical Sciences. vol. 93, Oct. 10, 2016, pp. 244-252.

Neal B. et al., (2017) Canagliflozin and cardiovascular and renal events in type 2 diabetes. N Engl J Med, 377(7), 644-657.

Nicholls, S. J. et al., "Effect of the BET Protein Inhibitor, RVX-208, on Progression of Coronary Atherosclerosis: Results of the Phase 2b, Randomized, Double-Blind, Multicenter, ASSURE Trial," Am J. Cardiovasc Drugs, © Springer International Publishing Switzerland 2015, 11 pgs. DOI 10.1007/s40256-015-0146-z.

Perkovic, V., et al. (2019) Canagliflozin and renal outcomes in type 2 diabetes and nephropathy. N Engl J Med, 380(24), 2295-2306.

Picaud, S. et al. "RVX-208, an inhibitor of BET transcriptional regulators with selectivity for the second bromodomain", PNAS, vol. 110, No. 49, 15 pgs., Dec. 3, 2013.

Rastogi, A. et al., (2017) SGLT2 Inhibitors Through the Windows of EMPA-REG and CANVAS Trials: A Review. Diabetes Ther, 8, 1245-1251.

Ray, K. K. et al., "Effect of selective BET protein inhibitor apabetalone on cardiovascular outcomes in patients with acute coronary syndrome and diabetes: Rationale, design, and baseline characteristics of the BETonMACE trial," Am. Heart J, 2019; 217:72-83, Copyright © 2019 Published by Elsevier, 12 pgs. https://doi.org/10.1016/j.ahj.2019.08.001.

Ray, K. K., et al., "Effect of Apabetalone Added to Standard Therapy on Major Adverse Cardiovascular Events in Patients With Recent Acute Coronary Syndrome and Type 2 Diabetes," JAMA, 2020, 323(16), 1565-1573 © 2020 American Medical Association, 9 pgs.

Siebel, A.L. et al. "Effects of the BET-Inhibitor, RVX-208 on the HDL Lipidome and Glucose Metabolism in Individuals with Prediabetes: A Randomized Controlled Trial," Metabolism Clinical and Experimental 65 (2016) 904-914, Accepted: Mar. 3, 2016, www.sciencedirect.com, http://dx.doi.org/10.1016/j.metabol.2016.03.002, © 2016 Elsevier Inc., 11 pgs.

Tsujikawa, L. M. et al: "Apabetalone (RVX-208) reduces vascular inflammation in vitro and in CVD patients by a BET-dependent epigenetic mechanism". Clinical Epigenetics, (2019) 11:102. https://doi.org/10.1186/s13148-019-0696-z.

Verma, S. et al., "SGLT2 Inhibitors and Mechanisms of Cardiovascular Benefit: A State-of-the-Art Review," Diabetologia, (2018) 61:2108-2117, https://doi.org/10.1007/s00125-018-4670-7, © Springer-Verlag GmbH Germany, part of Springer Nature 2018, Accepted: Apr. 23, 2018, Published online: Aug. 22, 2018, 10 pgs.

Wiviott, S.D. et al., (2019) Dapagliflozin and Cardiovascular Outcomes in Type 2 Diabetes. N Engl J Med, 380(4), 347-357.

Zinman, B. et al., (2015) Empagliflozin, cardiovascular outcomes, and mortality in type 2 diabetes. N Engl J Med, 373(22), 2117-28.

Alfaro-Alvarado, F.A. (2023) Association Between Sarcopenia and Poor Glycemic Control in Older Adults with Type 2 Diabetes Mellitus, Diseases 11, 175.

Bailey, R. A., et al. (2014) Chronic kidney disease in US adults with type 2 diabetes: an updated national estimate of prevalence based on Kidney Disease: Improving Global Outcomes (KDIGO) staging. BMC Res Notes, 7: 415, 1-7.

Bayarsaihan D. (2011) Epigenetic Mechanisms in Inflammation. Journal of Dental Research, 90(1), 9-17.

Beckman, J. A. and Creager, M.A. (2016) Vascular Complications of Diabetes. Circulation Research, 118, 1771-1785.

Bikbov, B., et al. (2020) GBD Chronic Kidney Disease Collaboration. Global, regional, and national burden of chronic kidney disease, 1990-2017: A systematic analysis for the Global Burden of Disease Study 2017. Lancet, 395, 709-733.

Brown, J. D., et al. (2014) NF-κB directs dynamic super enhancer formation in inflammation and atherogenesis. Molecular cell, 56(2), 219-231.

Chen, L. F., et al. (2005) NF-kappaB RelA phosphorylation regulates RelA acetylation. Molecular and cellular biology, 25(18), 7966-7975.

Cressman, M., et al. (2018) CKD Prevalence and Risk Are Higher in Adults with Type 2 vs. Type 1 Diabetes—An Assessment of 1.5 Million Patients Recently Evaluated in U.S. Clinical Practices. Diabetes, 67 (Supplement 1).

Das, S., et al. (2017) Regulation of angiotensin II actions by enhancers and super-enhancers in vascular smooth muscle cells. Nat Commun 8, 1467 (2017).

Davidson, J. A. (2019) SGLT2 inhibitors in patients with type 2 diabetes and renal disease: overview of current evidence. Postgrad Med, 131(4), 251-260.

Fowler, M. J. (2008) Microvascular and Macrovascular Complications of Diabetes. Clinical Diabetes, 26(2), 77-82.

Furukawa, S et al. "Medical Test", (古川聡子 ほか 医学検査 2018, 67(4), 563-567.

Heerspink, H. J. L., et al. (2020) Dapagliflozin in Patients with Chronic Kidney Disease. N Engl J Med, 383(15), 1436-1446.

Hill, N. R., et al. (2016) Global Prevalence of Chronic Kidney Disease—A Systematic Review and Meta-Analysis. PloS one, 11(7), e0158765.

Hsu, H. et al., (2024) Major adverse cardiovascular events' reduction and their association with glucose-lowering medications and glycemic control among patients with type 2 diabetes: A retrospective cohort study using electronic health records, Journal of Diabetes, 16, e13604.

Huang, B., et al. (2009) Brd4 coactivates transcriptional activation of NF-kappaB via specific binding to acetylated RelA. Molecular and cellular biology, 29(5), 1375-1387.

Kalantar-Zadeh, K. et al., Effect of Apabetalone on Cardiovascular Events in Diabetes, CKD, and Recent AcuteCoronary Syndrome Results from the BETonMACE Randomized Controlled Trial, Clinical Journal of the American Society of Nephrology 2021, vol. 16, No. 5, pp. 705-716, DOI: 10.2215/cjn.16751020.

Kassebaum, N. J., et al. (2016) GBD 2015 DALYs and HALE Collaborators. Global, regional, and national disability-adjusted life-years (DALYs) for 315 diseases and injuries and healthy life expectancy (HALE), 1990-2015: a systematic analysis for the Global Burden of Disease Study 2015. Lancet, 388(10053), 1603-58.

Khan, H.A., et al., "Association Between Glycaemic Control and Serum Lipids Profile in Type 2 Diabetic Patients: HbA1c Predicts Dyslipideaemia," 2007, Clin Exp Med 7:24-29.

Kulikowski, E., et al. (2017) Effects of Apabetalone (RVX-208) on Serum Albumin in Subjects with CVD, Diabetes and Chronic Kidney Disease; A Post-Hoc Analysis of the ASSURE and SUSTAIN Clinical Trials. Nephrology Dialysis Transplantation, 32(Supplement 3), iii264-iii278.

Levey, A. S. and Inker, L. A. (2016) GFR as the "Gold Standard": Estimated, Measured, and True. Am J Kidney Dis, (1), 9-12.

Levey, A. S., et al. (2020) Change in Albuminuria and GFR as End Points for Clinical Trials in Early Stages of CKD: A Scientific Workshop Sponsored by the National Kidney Foundation in Collaboration with the US Food and Drug Administration and European Medicines Agency. Am J Kidney Dis, 75(1), 84-104.

Martinez-Moreno, Julio M., et al., "Epigenetic Modifiers as Potential Therapeutic Targets n Diabetic Kidney Disease," Molecular Sciences, 2020, 21, 4113, 1-26.

Mosenzon, O., et al. (2019) Effects of dapagliflozin on development and progression of kidney disease in patients with type 2 diabetes:

(56) References Cited

OTHER PUBLICATIONS an analysis from the DECLARE-TIMI 58 randomised trial. Lancet Diabetes Endocrinol, 7(8), 606-617.

Perkovic, V., et al. (2018) Canagliflozin and renal outcomes in type 2 diabetes: results from the CANVAS Program randomised clinical trials. Lancet Diabetes Endocrinol, 6(9), 691-704.

Rangel, E. B., et al. (2019) Micro- and Macrovascular Complications in Diabetes Mellitus: Preclinical and Clinical Studies. J Diabetes Res, 2019, 2161085.

Ray, K.K., et al. (2019) BET-inhibition with Apabetalone in Post-ACS Patients with Diabetes: Design and Baseline Characteristics of the BETonMACE Trial, 40, 1-3.

Villagra, A., et al. (2010) Histone deacetylases and the immunological network: implications in cancer and inflammation. Oncogene, 29(2), 157-173.

Vithian, K. and Hurel, S. (2010) Microvascular complications: pathophysiology and management. Clin Med (Lond), 10(5), 505-509.

Wang, H., et al. (2016) GBD 2015 Mortality and Causes of Death Collaborators. Global, regional, and national life expectancy, all-cause mortality, and cause-specific mortality for 249 causes of death, 1980-2015: a systematic analysis for the Global Burden of Disease Study 2015. Lancet, 388(10053), 1459-544.

Wanner, C., et al. (2016) Empagliflozin and Progression of Kidney Disease in Type 2 Diabetes. N Engl J Med, 375, 323-334.

Zelnick, L. R, et al. (2017) Diabetes and CKD in the United States Population, 2009-2014. CJASN, 12 (12) 1984-1990.

p-value calculated using Mann-Whitney test for continuous variables,
RVX-208 treated patients receiving SGLT2 inhibitors vs. placebo treated patients receiving SGLT2 inhibitors p-value calculated rank-Analysis of Variance (ANOVA) non-parametric test using treatment arm as a factor,
RVX-208 treated patients receiving SGLT2 inhibitors vs. RVX-208 monotherapy p=0.002 (Rank-ANOVA)

p=0.05 (Mann-Whitney)

Median eGFR Change from Baseline to LVT (mL/min)

p=0.002 (Rank-ANOVA)

p=0.05 (Mann-Whitney)

Mean eGFR Change from Baseline to LVT (mL/min)

p-value calculated using Mann-Whitney test for continuous variables,
RVX-208 treated patients receiving SGLT2 inhibitors vs. placebo treated patients receiving SGLT2 inhibitors p-value calculated rank-Analysis of Variance (ANOVA) non-parametric test using treatment arm as a factor,
RVX-208 treated patients receiving SGLT2 inhibitors vs. RVX-208 monotherapy

METHODS FOR IMPROVING RENAL FUNCTION WITH A COMBINATION OF A BET BROMODOMAIN INHIBITOR AND A SODIUM DEPENDENT GLUCOSE TRANSPORT 2 INHIBITOR

This application is a national stage filing under 35 U.S.C. § 371 of International Application No. PCT/IB2021/060043, filed Oct. 29, 2021, which claims the benefit of priority of U.S. Provisional Application No. 63/107,853, filed Oct. 30, 2020, the entire disclosure of all of which are incorporated herein by reference in their entireties.

The present disclosure relates to methods for improving renal function or methods for treating and/or preventing a kidney disease or an associated disorder by administering to a subject in need thereof, a combination of a sodium-glucose transport protein 2 (SGLT2) inhibitor and a compound of Formula I or Ia or a stereoisomer, tautomer, pharmaceutically acceptable salt, or hydrate thereof.

According to the National Kidney Foundation, estimated glomerular filtration rate (eGFR) is the strongest non-invasive way to assess renal function and the stage of chronic kidney disease (CKD) (Levey and Inker 2016). Using a patient's blood creatinine level, age, body size, and gender, physicians can determine the stage of kidney disease and the most optimal treatment plan to improve the likelihood of reducing kidney disease and associated-disorders progression. Renal function decline is a hallmark marker of mortality risk. It is estimated that approximately 15% of US adults have some form of CKD (Hill et al. 2016). Kidney disease is now the twelfth leading cause of death globally. (Bikbov et al. 2020). The significance of this disease burden is further highlighted in the recent World Health Organization report which has recently positioned CKD as one of the most important non-communicable diseases in the world. The report highlights that CKD and worsening renal function impact several other high risk patient disease groups, and serve as a comorbidity for diabetes and hypertension, while also indirectly impacting global morbidity and mortality of leading causes of deaths, such as cardiovascular diseases, diabetes, hypertension, infection with human immunodeficiency virus (HIV), and malaria. The Global Burden of Disease study estimated that 1.2 million deaths, 19 million disability-adjusted life-years (DALYs) and 18 million years of life lost from cardiovascular diseases were directly attributable to reduced glomerular filtration rates (Kassenibaum et al. 2016; Wang et al. 2016). These data highlight the critical importance of renal function, and more specifically estimated glomerular filtration rate (eGFR), as a marker of risk and in mortality.

As such, the development of novel, safe, and orally active agents that improve renal function as shown by an increasing eGFR or increasing the eGFR slope remains an unmet need in order to complement the existing portfolio of standard of care therapies, including statins, beta blockers, platelet inhibitors, bone and mineral regulators, and the more recently introduced sodium dependent glucose transporter (referred to as SGLT2, herein) inhibitors. To date, the available treatments only slow the decline of eGFR. No treatment has been able to increase eGFR or eGFR slope in patients.

Increasing eGFR or slowing the rate of decline of eGFR in CKD patients is known to correlate with improving complications associated with CKD, and preventing progression to more severe stages of CKD (Levey et al 2020).

Diabetes, and especially type II diabetes (T2DM), is characterized by chronic elevated blood glucose levels.

Diabetes is associated with CKD as a comorbidity and several complications, such as nephropathy (Fowler 2008; Vithian and Hurel 2010; Beckman and Creager 2016; Rangel et al. 2016). Up to 40% of US adults with diagnosed T2DM have chronic kidney disease, resulting from diabetic nephropathy, of which over half have moderate to severe CKD (Bailey et al. 2014; Zelnick et al. 2017; Cressman et al. 2018).

The introduction of the SGLT2 inhibitors provided a potential new treatment option for patients with CKD. SGLT2 inhibitors reduce the secretion of glucose in the urine by inhibition of sodium glucose transport protein 2, and have been shown to reduce the decline of renal function in patients with established cardiovascular disease, diabetes, and chronic kidney disease (Zinman et al. 2015; Neal et al. 2017; Perkovic et al. 2019; Wiviott et al. 2019). The ability of SGLT2 inhibitors to reduce the decline of eGFR in T2DM patients has been studied in several clinical trials, such as EMPA-REG OUTCOME for empaglifozin (NCT01131676); CANVAS Program and CREDENCE for canaglifozin (NCT01032629, NCT01989754, and NCT02065791); and DECLARE-TIMI 58 (NCT01730534) for dapaglifozin. Although these trials provided some evidence of slowing the decline of renal function, none of them demonstrated any increase in eGFR, or consequently, any improvement of renal function versus baseline (Davidson 2019).

The DAPA-CKD study evaluated the effects of dapagliflozin in patients with CKD, with or without type 2 diabetes. Although the data from this study represented significant slowing of renal function decline, absolute values for eGFR over the 30 months treatment versus baseline measurements were −7.15 units in the dapagliflozin group and −9.47 units in the placebo group, thereby indicating that dapagliflozin was capable of slowing the renal function decline when compared to the placebo, but unable to increase eGFR (Heerspink et al. 2020).

To date, no combination of the standard of care therapies for chronic kidney disease (including statins, beta blockers, platelet inhibitors, bone and mineral regulators, and SGLT2 inhibitors) has reported any improvement of renal function in these patients. Specifically, there are no reports of renal function improvement versus baseline (manifested as an increase in eGFR) or renal slope improvement versus baseline (manifested as an increase eGFR slope) by any of these SGLT2 inhibitor molecules.

Apabetalone (RVX-208 or RVX000222), a compound of Formula I or Ia, is a first-in-class Bromodomain and Extra-Terminal (BET)-inhibitor (BETi) that binds selectively to the second bromodomain of BET proteins. BET proteins (BRD2, BRD3, BRD4, and BRDT) are epigenetic readers that recognize and bind to acetylated lysines on histones 3 and 4 and on some transcription factors. Histone bound BETs recruit transcription factors and machinery to gene enhancer and promoter sites, facilitating the transcription of proximal genes. Chronic disease profoundly alters the acetylation landscape (Chen et al. 2005; Villagra et al. 2010; Bayarsaihan 2011), relocating BET proteins to the super-enhancers and promoters of genes involved in inflammation, lipid metabolism, and vascular function (Huang et al. 2009; Brown et al. 2014; Das et al. 2017). Apabetalone prevents BET protein translocation, inhibiting the transcription of genes that drive chronic diseases. Apabetalone treatment, by targeting BET proteins, is characterized by multipronged effects which are augmented in conditions with more pronounced maladaptive BET regulation.

A recently completed clinical Phase 3 trial (BETon-MACE; NCT02586155) evaluated the effect on MACE of apabetalone (RVX-208) in type 2 diabetes patients with low HDL cholesterol (below 40 mg/dL for males and below 45 mg/dL for females) and a recent ACS (preceding 7-90 days). All patients received high intensity statin treatment. BETon-MACE was the first clinical trial to chronically dose high-risk cardiovascular disease patients with T2DM with the combination of a BET inhibitor and an SGLT2 inhibitor. In the same BETonMACE clinical trial, the effects of RVX-208 monotherapy, SGLT2 inhibitor monotherapy, and a combination therapy composed of RVX-208 and SGLT2 inhibitor on eGFR levels in T2DM patients with a recent ACS were also evaluated.

Prior to BETonMACE, in a post-hoc analysis of the phase 2 ASSURE (NCT01067820) and SUSTAIN (NCT01423188) clinical trials, patients with established cardiovascular disease and eGFR<60 mL/min/1.73 m² treated with RVX-208 monotherapy observed an increase in eGFR of 3.4% (p=0.04 vs. baseline) compared to a decrease of 5.9% in the placebo group (Kulikowski et al 2017). However, in further clinical analysis in the more recently completed BETonMACE trial, RVX-208 monotherapy did not demonstrate the ability to statistically improve eGFR versus placebo in T2DM patients with a recent ACS (Ray et al. 2020). No statistically significant improvements in eGFR were observed in the whole patient population (Ray et al. 2020). We also found in this study that SGLT2 inhibitor monotherapy did not improve eGFR.

Surprisingly, as detailed in Example 2, we found that patients treated with the combination of RVX-208 and an SGLT2 inhibitor showed pronounced improvement of renal function, as measured by eGFR, compared to treatment with either therapy alone. The summary of the results discussed below and in the detailed description of the results in Example 2 demonstrate that RVX-208 or SGLT2 inhibitors by themselves did not improve eGFR in patients with recent ACS and T2DM. However, when apabetalone was combined with a SGLT2 inhibitor, an unexpected and statistically significant increase of eGFR was observed, and this improvement exceeded the additive effects of RVX-208 and the SGLT2 inhibitor individually.

Of note, RVX-208 in combination with SGLT2 inhibitors increased eGFR from a median of 114 mL/min at baseline to a median of 120 mL/min at last visit on treatment (LVT). The SGLT2 inhibitor monotherapy had a median eGFR of 109 mL/min at baseline and a median eGFR of 110 mL/min at LVT (i.e., a modest increase in median eGFR). The RVX-208 monotherapy group had a median eGFR of 97 mL/min at baseline and a median eGFR of 96 mL/min at LVT (i.e., no increase in median eGFR).

Accordingly, the technical solution provided by the present disclosure includes methods of treating and/or preventing, including slowing the progression of, a kidney disease or an associated disorder or methods for improving renal function, as measured by an increase in estimated glomerular filtration rate (eGFR), comprising administering to a subject in need thereof, a combination of a sodium-glucose transport protein 2 (SGLT2) inhibitor and a compound of Formula I or a stereoisomer, tautomer, pharmaceutically acceptable salt, or hydrate thereof.

Compounds of Formula I have previously been described in U.S. Pat. No. 8,053,440, which is incorporated herein by reference. Compounds of Formula I include:

Formula I or stereoisomers, tautomers, pharmaceutically acceptable salts, or hydrates thereof, wherein:

$R_1$ and $R_3$ are each independently selected from alkoxy, alkyl, amino, halogen, and hydrogen;

$R_2$ is selected from alkoxy, alkyl, alkenyl, alkynyl, amide, amino, halogen, and hydrogen;

$R_5$ and $R_7$ are each independently selected from alkyl, alkoxy, amino, halogen, and hydrogen;

$R_6$ is selected from amino, amide, alkyl, hydrogen, hydroxyl, piperazinyl, and alkoxy;

W is selected from C and N, wherein:

if W is N, then p is 0 or 1, and if W is C, then p is 1; and for $W—(R_4)_p$, W is C, p is 1 and $R_4$ is H, or W is N and p is 0.

RVX-208 is a representative example of a compound of Formula I.

In some embodiments, the kidney disease or an associated disorder treated and/or prevented by a method of the disclosure is selected from a kidney disease associated with reduced eGFR (i.e., <60 mL/min/1.73 m²±10%). In some embodiments, the kidney disease associated with reduced eGFR is also associated with diabetes (type 2 diabetes or T2DM) and a diabetes-related disease or disorder associated with reduced eGFR. In one embodiment, the kidney disease associated with reduced eGFR is chronic kidney disease (including chronic kidney disease that is a comorbidity of type 2 diabetes). In one embodiment, the kidney disease associated with reduced eGFR is nephropathy (including diabetic nephropathy).

In some embodiments, the treating and/or preventing of the kidney disease or an associated disorder in a method of the disclosure reduces the decline of renal function, as assessed by increasing eGFR slope, for example, in a subject with T2DM or CKD.

In some embodiments, the treating and/or preventing of the kidney disease or an associated disorder in a method of the disclosure improves renal function, as defined by increasing eGFR slope, for example, in a subject with T2DM or CKD.

In some embodiments, the kidney disease or an associated disorder is treated and/or prevented by a method of the disclosure in a subject with T2DM or CKD.

In some embodiments, the compound of Formula I or Ia is administered simultaneously with a SGLT2 inhibitor. In some embodiments, the compound of Formula I is administered sequentially with the SGLT2 inhibitor. In some embodiments, the compound of Formula I is administered with the SGLT2 inhibitor as a single composition. In some embodiments, the compound of Formula I and the SGLT2 inhibitor are administered as separate compositions.

In some embodiments, the compound of Formula Ia is selected from

Formula Ia or a stereoisomer, tautomer, pharmaceutically acceptable salt, or hydrate thereof, wherein:

$R_1$ and $R_3$ are each independently selected from alkoxy, alkyl, and hydrogen;

$R_2$ is selected from alkoxy, alkyl, and hydrogen;

$R_5$ and $R_7$ are each independently selected from alkyl, alkoxy, and hydrogen;

$R_6$ is selected from alkyl, hydroxyl, and alkoxy;

W is selected from C and N, wherein:

if W is N, then p is 0 or 1, and if W is C, then p is 1; and for W—$(R_4)_p$, W is C, p is 1 and $R_4$ is H, or W is N and p is 0.

In some embodiments, the compound of Formula I or Ia is 2-(4-(2-hydroxyethoxy)-3,5-dimethylphenyl)-5,7-dimethoxyquinazolin-4(3H)-one (RVX-208 or RVX000222) or a pharmaceutically acceptable salt thereof.

In some embodiments, the daily dose of a compound of Formula I or Ia, or 2-(4-(2-hydroxyethoxy)-3,5-dimethylphenyl)-5,7-dimethoxyquinazolin-4(3H)-one, or a pharmaceutically acceptable salt of any of the foregoing is between 100-300 mg, e.g., 200 mg.

In some embodiments, the compound of Formula I or Ia is given once a day. In some embodiments, it is given twice a day.

In some embodiments, the SGLT2 inhibitor is empagliflozin, canagliflozin, dapagliflozin, remogliflozin, ipragliflozin, bexagliflozin, ertugliflozin, sotagliflozin, luseogliflozin, tofogliflozin, or HM41322.

In some embodiments, the SGLT2 inhibitor is empagliflozin, canagliflozin, or dapagliflozin.

In some embodiments, the SGLT2 inhibitor is dapagliflozin.

In some embodiments, the daily dose of dapagliflozin is between 5-10 mg.

In some embodiments, the daily dose of dapagliflozin is 5 mg or 10 mg.

DEFINITIONS

Figure 1:
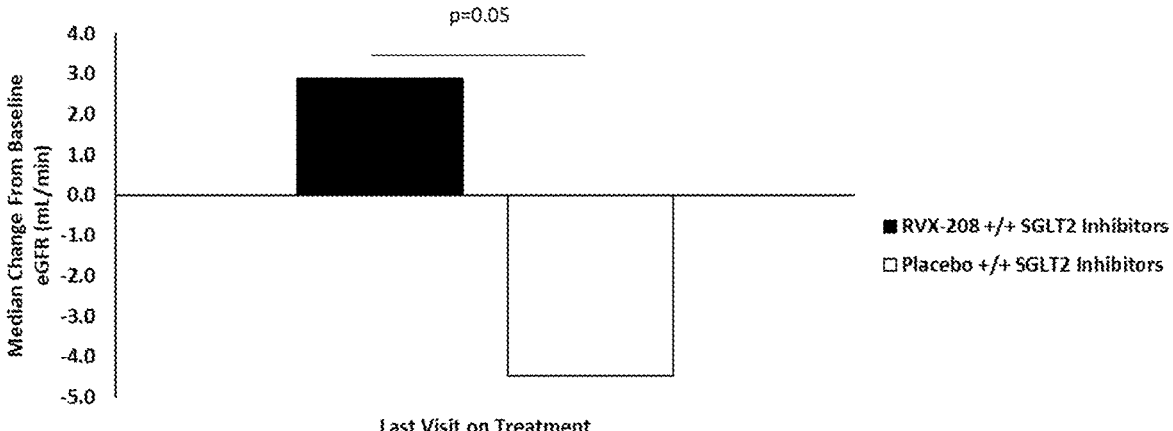
FIG. 1 depicts a comparison of the change of eGFR from baseline to LVT in patients administered RVX-208 with SGLT2 inhibitors versus patients administered placebo with SGLT2 inhibitors.

By "optional" or "optionally," is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible, and/or inherently unstable.

As used herein, the term "hydrate" refers to a crystal form with either a stoichiometric or non-stoichiometric amount of water incorporated into the crystal structure.

The term "alkenyl" as used herein refers to an unsaturated straight or branched hydrocarbon having at least one carbon-carbon double bond, such as a straight or branched group of 2-8 carbon atoms, referred to herein as $(C_2-C_8)$ alkenyl. Exemplary alkenyl groups include, but are not limited to, vinyl, allyl, butenyl, pentenyl, hexenyl, butadienyl, pentadienyl, hexadienyl, 2-ethylhexenyl, 2 propyl 2-butenyl, and 4-(2-methyl-3-butene)-pentenyl.

The term "alkoxy" as used herein refers to an alkyl group attached to an oxygen (O-alkyl). "Alkoxy" groups also include, but are not limited to, an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-8 carbon atoms, referred to herein as $(C_1-C_8)$ alkoxy. Exemplary alkoxy groups include, but are not limited to, methoxy and ethoxy.

The term "alkyl" as used herein refers to a saturated straight or branched hydrocarbon, such as a straight or branched group of 1-8 carbon atoms, referred to herein as $(C_1-C_8)$ alkyl. Exemplary alkyl groups include, but are not limited to, methyl, ethyl, propyl, isopropyl, 2-methyl-1-propyl, 2-methyl-2-propyl, 2-methyl-1-butyl, 3 methyl-1-butyl, 2-methyl-3-butyl, 2,2-dimethyl-1-propyl, 2-methyl-1-pentyl, 3 methyl-1-pentyl, 4-methyl-1-pentyl, 2-methyl-2-pentyl, 3-methyl-2-pentyl, 4 methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "amide" as used herein refers to the form $NR_aC(O)(R_b)$ or $C(O)NR_bR_c$, wherein $R_a$, $R_b$, and $R_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_b$, or $R_c$. The amide also may be cyclic, for example, $R_b$ and $R_c$ may be joined to form a 3- to 8-membered ring, such as a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., amide-COOH or salts such as amide-COONa, an amino group attached to a carboxy group (e.g., amino-COOH or salts such as amino-COONa).

The term "amine" or "amino" as used herein refers to the form $NR_dR_e$ or $N(R_d)R_e$, wherein $R_d$ and $R_e$ are independently selected from alkyl, alkenyl, alkynyl, aryl, arylalkyl, carbamate, cycloalkyl, haloalkyl, heteroaryl, heterocycle, and hydrogen. The amino can be attached to the parent molecular group through the nitrogen. The amino also may be cyclic, for example any two of $R_d$ and $R_e$ may be joined together or with the N to form a 3- to 12-membered ring (e.g., morpholino or piperidinyl). The term amino also includes the corresponding quaternary ammonium salt of any amino group. Exemplary amino groups include, but are not limited to, alkylamino groups, wherein at least one of $R_d$ and $R_e$ is an alkyl group. In some embodiments, $R_d$ and $R_e$ each may be optionally substituted with hydroxyl, halogen, alkoxy, ester, or amino.

The term "aryl" as used herein refers to a mono-, bi-, or other multi carbocyclic, aromatic ring system. The aryl group can optionally be fused to one or more rings selected from aryls, cycloalkyls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to, a monocyclic aromatic ring system, wherein the ring comprises 6 carbon atoms, referred to herein as "($C_6$) aryl."

The term "arylalkyl" as used herein refers to an alkyl group having at least one aryl substituent (e.g., aryl-alkyl). Exemplary arylalkyl groups include, but are not limited to, arylalkyls having a monocyclic aromatic ring system, wherein the ring comprises 6 carbon atoms, referred to herein as "($C_6$) arylalkyl."

The term "carbamate" as used herein refers to the form $R_gOC(O)N(R_h)$, $R_gOC(O)N(R_h)R_i$, or $OC(O)NR_hR_i$, wherein $R_g$, $R_h$, and $R_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_g$, $R_h$ and $R_i$ are independently selected from aryl and heteroaryl, such as pyridine, pyridazine, pyrimidine, and pyrazine).

The term "carbocycle" as used herein refers to an aryl or cycloalkyl group.

The term "carboxy" as used herein refers to COOH or its corresponding carboxylate salts (e.g., COONa). The term carboxy also includes "carboxycarbonyl," e.g., a carboxy group attached to a carbonyl group, e.g., C(O)—COOH or salts, such as C(O)—COONa.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include, but are not limited to, alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide, and thioketone. Dicarboxylic acids include, but are not limited to, succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure C(O)O—, C(O)OR_j, $R_kC(O)O—R_j$, or $R_kC(O)O—$, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen, but $R_j$ cannot be hydrogen. The ester may be cyclic, for example, the carbon atom and $R_j$, the oxygen atom and $R_k$, or $R_j$ and $R_k$ may be joined to form a 3- to 12-membered ring. Exemplary esters include, but are not limited to, alkyl esters wherein at least one of $R_j$ and $R_k$ is alkyl, such as O—C(O) alkyl, C(O)—O-alkyl, and alkyl C(O)—O-alkyl. Exemplary esters also include, but are not limited to, aryl or heteroaryl esters, e.g., wherein at least one of $R_j$ and $R_k$ is a heteroaryl group such as pyridine, pyridazine, pyrimidine and pyrazine, such as a nicotinate ester. Exemplary esters also include, but are not limited to, reverse esters having the structure $R_kC(O)O—$, where the oxygen is bound to the parent molecule. Exemplary reverse esters include, but are not limited to, succinate, D-argininate, L-argininate, L-lysinate, and D-lysinate. Esters also include carboxylic acid anhydrides and acid halides.

The terms "halo" or "halogen" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1 to 3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "$(C_2-C_5)$ heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include, but are not limited to, acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure $C(O)$—$R_n$ (such as acetyl, $C(O)CH_3$) or $R_n$—$C(O)$—$R_o$. The ketone can be attached to another group through $R_n$ or $R_o$. $R_n$ and $R_o$ can be alkyl, alkenyl, alkynyl, cycloalkyl, heterocyclyl or aryl, or $R_n$ and $R_o$ can be joined to form a 3- to 12 membered ring.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide and thioketone.

The term "thioalkyl" as used herein refers to an alkyl group attached to a sulfur (S-alkyl).

"Alkyl," "alkenyl," "alkynyl", "alkoxy", "amino" and "amide" groups can be optionally substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide, thioketone, ureido, and N.

The substituents may be branched to form a substituted or unsubstituted heterocycle or cycloalkyl.

As used herein, a suitable substitution on an optionally substituted substituent refers to a group that does not nullify the synthetic or pharmaceutical utility of the compounds of the present disclosure or the intermediates useful for preparing them. Examples of suitable substitutions include, but are not limited to: $C_1-C_8$ alkyl, $C_2-C_8$ alkenyl or alkynyl; $C_6$ aryl, 5- or 6-membered heteroaryl; $C_3-C_7$ cycloalkyl; $C_1-C_8$ alkoxy; $C_6$ aryloxy; CN; OH; oxo; halo, carboxy; amino, such as $NH(C_1-C_8$ alkyl), $N(C_1-C_8$ alkyl$)_2$, $NH((C_6)$aryl), or $N((C_6)$aryl$)_2$; formyl; ketones, such as $CO(C_1-C_8$ alkyl), —$CO((C_6$ aryl) esters, such as $CO_2(C_1-C_8$ alkyl) and $CO_2$ ($C_6$ aryl). One of skill in art can readily choose a suitable substitution based on the stability and pharmacological and synthetic activity of the compound of the present disclosure.

The term "pharmaceutically acceptable composition" as used herein refers to a composition comprising at least one compound as disclosed herein formulated together with one or more pharmaceutically acceptable carriers.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The term "pharmaceutically acceptable composition" as used herein, refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of Formula I or Ia. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include, but are not limited to, alkali metal or alkaline earth metal salts and, particularly, calcium, magnesium, sodium, lithium, zinc, potassium, and iron salts.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The compounds of Formula I or Ia may contain one or more chiral centers and/or double bonds and, therefore, exist as stereoisomers, such as geometric isomers, enantiomers, or diastereomers. The term "stereoisomers" when used herein consists of all geometric isomers, enantiomers, or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds for use in the methods of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of Formula I or Ia. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds of Formula I or Ia disclosed herein may exist as tautomers and both tautomeric forms are intended to be encompassed by the scope of the present disclosure, even though only one tautomeric structure is depicted.

As used herein, the term "SGLT2 inhibitor" refers a substance, such as a small molecule organic chemistry compound (≤1 kDa) or a large biomolecule such as a peptide (e.g., a soluble peptide), protein (e.g., an antibody), nucleic acid (e.g., siRNA) or a conjugate combining any two or more of the foregoing, that possesses the activity of inhibiting sodium-glucose transport protein 2 (SGLT2). Non-limiting examples of SGLT2 inhibitors include empagliflozin, canagliflozin, dapagliflozin, remogliflozin, ipragliflozin, HM41322, bexagliflozin, ertugliflozin, sotagliflozin, luseogliflozin, tofogliflozin, or a pharmaceutically acceptable salt of any of the foregoing. Additional examples of SGLT2 inhibitors are disclosed in WO01/027128, WO04/013118, WO04/080990, EP1852439A1, WO01/27128, WO03/099836, WO2005/092877, WO2006/034489, WO2006/064033, WO2006/1 17359, WO2006/117360, WO2007/025943, WO2007/028814, WO2007/031 548, WO2007/093610, WO2007/128749, WO2008/049923, WO2008/055870, and WO2008/055940, each of which is incorporated herein by reference in its entirety.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, either physically, e.g., stabilization of a discernible symptom, physiologically, e.g., stabilization of a physical parameter, or both. In yet another embodiment, "treatment" or "treating" refers to delaying the onset or progression of a disease or disorder. For example, treating a cholesterol disorder may comprise decreasing blood cholesterol levels.

As used herein, "prevention" or "preventing" refers to a reduction of the risk of acquiring a given disease or disorder or a symptom of a given disease or disorder.

As used herein, "diabetes-related disease or disorder" refers to a complication of type 2 diabetes and/or comorbidity of type 2 diabetes, whereby a subject suffering therefrom has an eGFR, as determined by blood or serum creatinine levels, age, body size, and gender, of <60 mL/min/1.73 m$^2$±10% (i.e., 54-66 mL/min/1.73 m$^2$), if or when calculated. Non-limiting examples of a diabetes-related disease or disorder as defined herein are diabetic nephropathy, chronic kidney disease that is a comorbidity of type 2 diabetes, and a combination thereof.

As used herein, "kidney disease or an associated disorder" refers to a kidney disease associated with reduced eGFR. In some embodiments, the kidney disease or associated disorder is also associated with diabetes (type 2 diabetes), or a diabetes-related disease or disorder. Non-limiting examples of a kidney disease associated with reduced eGFR include chronic kidney disease, nephropathy (e.g., C1a nephropathy, combination antiretroviral (cART) related-nephropathy, oxalate nephropathy), acute kidney failure or acute kidney injury, Alport syndrome, glomerulopathy (e.g., C3 glomerulopathy, C3 glomerulopathy with monoclonal gammopathy, C4 glomerulopathy), cardiorenal syndrome, Charcot-Marie-Tooth disease with glomerulopathy, congenital nephrotic syndrome, congestive renal failure, coronavirus (COVID-19) associated kidney failure and kidney disease, Fabry's diseases, diabetic kidney disease, glomerular diseases, glycosuria, hemolytic uremic syndrome (HUS), atypical hemolytic uremic syndrome (aHUS), hypercalcemia, hyperkalemia, hypocalcemia, kidney stones, nephrolithiasis, lupus kidney disease, lupus nephritis, malignancy-associated renal disease, malignant hypertension, Marfan syndrome and kidney disease, polycystic kidney disease, proteinuria (protein in urine), renal artery stenosis, renal osteodystrophy, kidney disease following hematopoietic cell transplantation, kidney disease related to stem cell transplantation, and uremia.

As used herein, "chronic kidney disease" refers to the gradual loss of kidney function, that being the ability of the kidneys to filter wastes and excess fluids from the blood, to be excreted in urine.

As used herein, "renal function" refers to kidney function as measured by estimated glomerular filtration rate (eGFR) and/or the eGFR slope. To improve renal function means to increase the eGFR and/or to increase the eGFR slope.

EXEMPLARY EMBODIMENTS

In one embodiment, the present disclosure provides a method for improving renal function or a method for treating and/or preventing, including slowing the progression of, a kidney-related disease or an associated disorder, as measured by an increase in estimated glomerular filtration rate (eGFR), wherein the method comprises administering to a subject in need thereof, a combination of a sodium-glucose transport protein 2 (SGLT2) inhibitor and a compound of Formula I:

Formula I or a stereoisomer, tautomer, pharmaceutically acceptable salt, or hydrate thereof, wherein:

$R_1$ and $R_3$ are each independently selected from alkoxy, alkyl, amino, halogen, and hydrogen;

$R_2$ is selected from alkoxy, alkyl, alkenyl, alkynyl, amide, amino, halogen, and hydrogen;

$R_5$ and $R_7$ are each independently selected from alkyl, alkoxy, amino, halogen, and hydrogen;

$R_6$ is selected from amino, amide, alkyl, hydrogen, hydroxyl, piperazinyl, and alkoxy;

W is selected from C and N, wherein:

if W is N, then p is 0 or 1, and if W is C, then p is 1; and for $W—(R_4)_p$, W is C, p is 1 and $R_4$ is H, or W is N and p is 0.

In one embodiment, the compound of Formula I is a compound of Formula Ia:

Formula Ia or a stereoisomer, tautomer, pharmaceutically acceptable salt, or hydrate thereof, wherein:

$R_1$ and $R_3$ are each independently selected from alkoxy, alkyl, and hydrogen;

$R_2$ is selected from alkoxy, alkyl, and hydrogen;

$R_5$ and $R_7$ are each independently selected from alkyl, alkoxy, amino, halogen, and hydrogen;

$R_6$ is selected from alkyl, hydroxyl, and alkoxy;

W is selected from C and N, wherein:

if W is N, then p is 0 or 1, and if W is C, then p is 1; and for $W—(R_4)_p$, W is C, p is 1 and $R_4$ is H, or W is N and p is 0.

In one embodiment, the compound of Formula I or Ia is 2-(4-(2-hydroxyethoxy)-3,5-dimethylphenyl)-5,7-dimethoxyquinazolin-4(3H)-one (RVX-208 or RVX000222) or a pharmaceutically acceptable salt thereof.

In one embodiment, the method comprises administering to the subject, a daily dose of 100-300 mg of 2-(4-(2-hydroxyethoxy)-3,5-dimethylphenyl)-5,7-dimethoxyquinazolin-4(3H)-one or an equivalent amount of a pharmaceutically acceptable salt thereof.

In one embodiment, the method comprises administering to the subject, a daily dose of 200 mg daily of 2-(4-(2-hydroxyethoxy)-3,5-dimethylphenyl)-5,7-dimethoxyquinazolin-4(3H)-one or an equivalent amount of a pharmaceutically acceptable salt thereof.

In one embodiment, the SGLT2 inhibitor is selected from empagliflozin, canagliflozin, dapagliflozin, bexagliflozin, ertugliflozin, sotagliflozin, luseogliflozin, tofogliflozin, and HM41322.

In one embodiment, the SGLT2 inhibitor is selected from empagliflozin, canagliflozin, and dapagliflozin.

In one embodiment, the compound of Formula I or Ia is administered simultaneously with the SGLT2 inhibitor as separate compositions.

In one embodiment, the compound of Formula I or Ia is administered with the SGLT2 inhibitor as a single composition.

In one embodiment, the subject is a human.

In one embodiment, the subject is a human on statin therapy. In one embodiment, the subject is a human on high intensity or maximum tolerated statin therapy. In one embodiment, the high intensity statin treatment or therapy refers to a daily dose of at least 20 mg, or at least 40 mg, or 20-80 mg, or 20-40 mg, or 40-80 mg. In one embodiment, the maximum tolerated statin treatment or therapy refers to a daily lose of at least 40 mg, or 40 mg-80 mg, or 80 mg. In one embodiment, the subject is on rosuvastatin therapy. In one embodiment, the subject is on atorvastatin therapy.

In one embodiment, the subject is a human with type 2 diabetes or chronic kidney disease. In one embodiment, the subject is a human with low HDL cholesterol (below 40 mg/dL for males and below 45 mg/dL for females) and a recent acute coronary syndrome (ACS) (preceding 7-90 days).

In one embodiment, the kidney disease or an associated disorder is a kidney disease associated with reduced eGFR, for example, in a subject with type 2 diabetes or chronic kidney disease.

In one embodiment, the kidney disease associated with reduced eGFR is associated with type 2 diabetes or a diabetes-related disease or disorder.

In one embodiment, the kidney disease associated with reduced eGFR is nephropathy. In one embodiment, the kidney disease associated with reduced eGFR is diabetic nephropathy.

In one embodiment, the kidney disease associated with reduced eGFR is chronic kidney disease. In one embodiment, the chronic kidney disease that is a comorbidity of type 2 diabetes.

In one embodiment, the method improves renal function by increasing eGFR slope, for example, in a subject with type 2 diabetes or chronic kidney disease.

In one embodiment, the method reduces the decline of renal function by increasing eGFR slope, for example, in a subject with type 2 diabetes or chronic kidney disease.

In one embodiment, the present disclosure provides a method for improving renal function by increasing the estimated glomerular filtration rate (eGFR), the method comprising administering to a subject in need thereof, a combination of a sodium-glucose transport protein 2 (SGLT2) inhibitor and a compound of Formula I or Formula Ia or a stereoisomer, tautomer, pharmaceutically acceptable salt, or hydrate thereof as defined above. In another embodiment, the present disclosure provides a method for increasing estimated glomerular filtration rate (eGFR), the method comprising administering to a subject in need thereof, a combination of a sodium-glucose transport protein 2 (SGLT2) inhibitor and a compound of Formula I or Formula Ia or a stereoisomer, tautomer, pharmaceutically acceptable salt, or hydrate thereof as defined above. In one embodiment, the method for improving renal function or the method for increasing the eGFR treats and/or prevents a kidney disease or associated disorder. Exemplary embodiments of the method for improving renal function or the method for increasing the eGFR, such as specific compounds of Formula I or Ia or a stereoisomer, tautomer, pharmaceutically acceptable salt, or hydrate thereof; specific daily doses of compounds of Formula I or Ia or a stereoisomer, tautomer, pharmaceutically acceptable salt, or hydrate thereof; specific SGLT2 inhibitors; manner of administration of compounds of Formula I or Ia or a stereoisomer, tautomer, pharmaceutically acceptable salt, or hydrate thereof and the SGLT2 inhibitor (i.e., simultaneously, sequentially, as separate compositions, or as a single composition); subject criteria, subject sub-populations; and specific diabetes-related diseases and disorders are as described in any one or more of the exemplary embodiments above.

REFERENCES

1. Levey, A. S. and Inker, L. A. (2016). GFR as the "Gold Standard": Estimated, Measured, and True. Am J Kidney Dis, (1), 9-12.
2. Hill, N. R., Fatoba, S. T., Oke, J. L., Hirst, J. A., O'Callaghan, C. A., Lasserson, D. S., & Hobbs, F. D.

16

(2016). Global Prevalence of Chronic Kidney Disease—A Systematic Review and Meta-Analysis. PloS one, 11(7), e0158765.
3. Bikbov, B., Purcell, C. A., Levey, A. S., et al. (2020). GBD Chronic Kidney Disease Collaboration. Global, regional, and national burden of chronic kidney disease, 1990-2017: A systematic analysis for the Global Burden of Disease Study 2017. Lancet, 395, 709-733.
4. Bailey, R. A., Wang, Y., Zhu, V., and Rupnow, M. FT. (2014). Chronic kidney disease in US adults with type 2 diabetes: an updated national estimate of prevalence based on Kidney Disease: Improving Global Outcomes (KDIGO) staging. BMC Res Notes, 7: 415.
5. Zelnick, L. R, Weiss, N. S., Kestenbaum, B. R., et al. (2017). Diabetes and CKD in the United States Population, 2009-2014. CJASN, 12 (12) 1984-1990
6. Cressman, M., Ennis, J. L., Goldstein, B. J. et al. (2018). CKD Prevalence and Risk Are Higher in Adults with Type 2 vs. Type 1 Diabetes—An Assessment of 1.5 Million Patients Recently Evaluated in U.S. Clinical Practices. Diabetes, 67 (Supplement 1)
7. Kassebaum, N. J., Arora, M., Barber, R. M., et al. (2016). GBD 2015 DALYs and HALE Collaborators. Global, regional, and national disability-adjusted life-years (DALYs) for 315 diseases and injuries and healthy life expectancy (HALE), 1990-2015: a systematic analysis for the Global Burden of Disease Study 2015. Lancet, 388(10053), 1603-58.
8. Wang, H., Naghavi, M., Allen, C., et al. (2016). GBD 2015 Mortality and Causes of Death Collaborators. Global, regional, and national life expectancy, all-cause mortality, and cause-specific mortality for 249 causes of death, 1980-2015: a systematic analysis for the Global Burden of Disease Study 2015. Lancet, 388 (10053), 1459-544.
9. Levey, A. S., Gansevoort, R. T., Coresh, J., et al. (2020). Change in Albuminuria and GFR as End Points for Clinical Trials in Early Stages of CKD: A Scientific Workshop Sponsored by the National Kidney Foundation in Collaboration with the US Food and Drug Administration and European Medicines Agency. Am J Kidney Dis, 75(1), 84-104.
10. Fowler, M. J. (2008). Microvascular and Macrovascular Complications of Diabetes. Clinical Diabetes, 26(2), 77-82.
11. Vithian, K. and Hurel, S. (2010). Microvascular complications: pathophysiology and management. Clin Med (Lond), 10(5), 505-509.
12. Beckman, J. A. and Creager, M. A. (2016). Vascular Complications of Diabetes. Circulation Research, 118, 1771-1785.
13. Rangel, E. B, Rodrigues, C. O., and de Sa, J. R. (2019). Micro- and Macrovascular Complications in Diabetes Mellitus: Preclinical and Clinical Studies. J Diabetes Res, 2019, 2161085.
14. Zinman, B., Wanner, C., Lachin, J. M., et al. (2015). Empagliflozin, cardiovascular outcomes, and mortality in type 2 diabetes. N Engl J Med, 373(22), 2117-2128.
15. Neal B., Perkovic V., Mahaffey, K. W., et al. (2017). Canagliflozin and cardiovascular and renal events in type 2 diabetes. N Engl J Med, 377(7), 644-657.
16. Perkovic, V., de Zeeuw, D., Mahaffey, K. W., et al. (2018). Canagliflozin and renal outcomes in type 2 diabetes: results from the CANVAS Program randomised clinical trials. Lancet Diabetes Endocrinol, 6(9), 691-704.

17. Perkovic, V., Jardine, M. J., Neal, B., et al. (2019). Canagliflozin and renal outcomes in type 2 diabetes and nephropathy. N Engl J Med, 380(24), 2295-2306.

18. Wiviott, S. D., Raz, I., Bonaca, M. P., et al. (2019). Dapagliflozin and Cardiovascular Outcomes in Type 2 Diabetes. N Engl J Med, 380(4), 347-357.

19. Wanner, C., Inzucchi, S. E., Lachin, J. M., et al. (2016). Empagliflozin and Progression of Kidney Disease in Type 2 Diabetes. N Engl J Med, 375,323-334.

20. Mosenzon, O., Wiviott, S. D., Cahn, A., et al. (2019). Effects of dapagliflozin on development and progression of kidney disease in patients with type 2 diabetes: an analysis from the DECLARE-TIMI 58 randomised trial. Lancet Diabetes Endocrinol, 7(8), 606-617.

21. Davidson, J. A. (2019). SGLT2 inhibitors in patients with type 2 diabetes and renal disease: overview of current evidence. Postgrad Med, 131(4), 251-260.

22. Heerspink, H. J. L., Stefansson, B. V., Correa-Rotter, R., et al. (2020). Dapagliflozin in Patients with Chronic Kidney Disease. N Engl J Med, 383(15), 1436-1446.

23. Chen, L. F., Williams, S. A., Mu, Y., Nakano, H., Duerr, J. M., Buckbinder, L., & Greene, W. C. (2005). NF-kappaB RelA phosphorylation regulates RelA acetylation. Molecular and cellular biology, 25(18), 7966-7975.

24. Villagra, A., Sotomayor, E. M., & Seto, E. (2010). Histone deacetylases and the immunological network: implications in cancer and inflammation. Oncogene, 29(2), 157-173.

25. Bayarsaihan D. (2011). Epigenetic mechanisms in inflammation. Journal of dental research, 90(1), 9-17.

26. Huang, B., Yang, X. D., Zhou, M. M., Ozato, K., & Chen, L. F. (2009). Brd4 coactivates transcriptional activation of NF-kappaB via specific binding to acetylated RelA. Molecular and cellular biology, 29(5), 1375-1387.

27. Brown, J. D., Lin, C. Y., Duan, Q., Griffin, G., Federation, A., Paranal, R. M., Bair, S., Newton, G., Lichtman, A., Kung, A., Yang, T., Wang, H., Luscinskas, F. W., Croce, K., Bradner, J. E., & Plutzky, J. (2014). NF-κB directs dynamic super enhancer formation in inflammation and atherogenesis. Molecular cell, 56(2), 219-231.

28. Das, S., Senapati, P., Chen, Z., et al. (2017). Regulation of angiotensin II actions by enhancers and super-enhancers in vascular smooth muscle cells. Nat Commun 8, 1467 (2017).

29. Kulikowski, E., Halliday, C., Lebioda, K., et al. (2017). Effects of Apabetalone (RVX-208) on Serum Albumin in Subjects with CVD, Diabetes and Chronic Kidney Disease; A Post-Hoc Analysis of the ASSURE and SUSTAIN Clinical Trials. Nephrology Dialysis Transplantation, 32 (Supplement 3), iii264-iii278.

EXAMPLES

Example 1: Clinical Development

Apabetalone (RVX-208) was evaluated in a recently completed clinical Phase 3 trial (BETonMACE; NCT02586155) for the effect on MACE in type 2 diabetes patients with low HDL cholesterol (below 40 mg/dL for males and below 45 mg/dL for females) and a recent acute coronary syndrome (ACS) (preceding 7-90 days). All patients received high intensity statin treatment or maximum tolerated statin treatment, which was 20-40 mg daily or a maximum daily dose of 40 mg for rosuvastatin or 40-80 mg daily or a maximum daily dose of 80 mg for atorvastatin.

Patients (n=2425) with ACS in the preceding 7 to 90 days, with type 2 diabetes and low HDL cholesterol (≤40 mg/dl for men, <45 mg/dl for women), receiving intensive or maximum-tolerated therapy with atorvastatin or rosuvastatin, were assigned in double-blind fashion to receive apabetalone 100 mg orally twice daily or matching placebo. Baseline characteristics include female sex (25%), myocardial infarction as index ACS event (74%), coronary revascularization for index ACS (76%), treatment with dual anti-platelet therapy (87%) and renin-angiotensin system inhibitors (91%), median LDL cholesterol 65 mg per deciliter, and median HbA1c 7.3%. The primary efficacy measure is time to first occurrence of cardiovascular death, non-fatal myocardial infarction, or stroke. The study enrolled 2425 patients and the MACE outcome population consisted of 2418 patients.

Example 2: Post-Hoc Analysis

In the BETonMACE clinical study, a total of N=298 patients (N=150 in RVX-208 treatment group and N=148 in placebo treatment group) were administered an SGLT2 inhibitor (empagliflozin, dapagliflozin, or canagliflozin) in addition to RVX-208 with specified statin therapy (atorvastatin and rosuvastatin) and other guideline-defined treatments. Specifically, a total of 150 patients received both RVX-208 and an SGLT2 inhibitor; a total of 148 received an SGLT2 inhibitor, but no RVX-208; a total of 1062 received RVX-208, but no SGLT2 inhibitor; a total of 1058 received neither RVX-208 or an SGLT2 inhibitor.

Patients who were randomized and received at least one dose of SGLT2 treatment while actively receiving study drug (RVX-208 or placebo) were counted as those receiving a combination of SGLT2 treatment with either RVX-208 or placebo. Patients receiving more than one drug therapy within the SGLT2 inhibitor class were counted only once based upon whichever drug therapy patients continued taking at the end of treatment with study drug (RVX-208 or placebo). In cases where patients were receiving more than one drug therapy within the SGLT2 inhibitor class at the end of treatment with study drug, whichever SGLT2 inhibitor therapy was received for longer was counted.

Estimated glomerular filtration rate (eGFR) was calculated by the central lab using serum creatinine values and the Cockcroft-Gault formula. Serum creatinine was collected as part of the chemistry panel at the following time points: baseline, week 24, week 52, week 76, week 100, and last visit on treatment (LVT). The Cockcroft-Gault formula requires the input of an individual's age, sex, and weight. The last visit on treatment (LVT) timepoint represented the longest study exposure duration for patients receiving RVX-208 or placebo with and without SGLT2 inhibitors and is the focus of this analysis. The median time to LVT (and study drug exposure) for patients with a baseline and LVT measurements for eGFR administered an SGLT2 inhibitor (N=298) was 742 days (2.03 years). For the patients treated with a SGLT2 inhibitor and RVX-208 (N=150), the median time to LVT was 748 days (2.05 years) and for the patients treated with a SGLT2 inhibitor and received placebo (N=148), the median time to LVT was 734 days (2.01 years). No statistical difference was observed between the duration of study drug exposure, indicating a balance was observed between treatment groups. At the LVT timepoint, a total of N=121 patients in the apabetalone treatment group and N=122 patients in the placebo group had eGFR measurements.

Change in eGFR in the patient population receiving the combination of an SGLT2 inhibitor in addition to RVX-208, the combination of an SGLT2 inhibitor in addition to placebo, and RVX-208 without an SGLT2 inhibitor was assessed from baseline to LVT.

In patients receiving an SGLT2 inhibitor in addition to RVX-208 (N=150), the median age was 58 years, 16% were women, 92% were white, mean duration of diabetes was 9.9 years, the average BMI was 30.3 kg/m$^2$ and the baseline eGFR was 114 mL/min.

In patients receiving an SGLT2 inhibitor in addition to placebo (N=148), the median age was 59 years, 18% were women, 89% were white, mean duration of diabetes was 10.6 years, the average BMI was 30.2 kg/m$^2$, and the baseline eGFR was 109 mL/min.

No statistical difference was observed in any of these parameters indicating a balance was observed between treatment groups.

Change in eGFR

Figure 2:
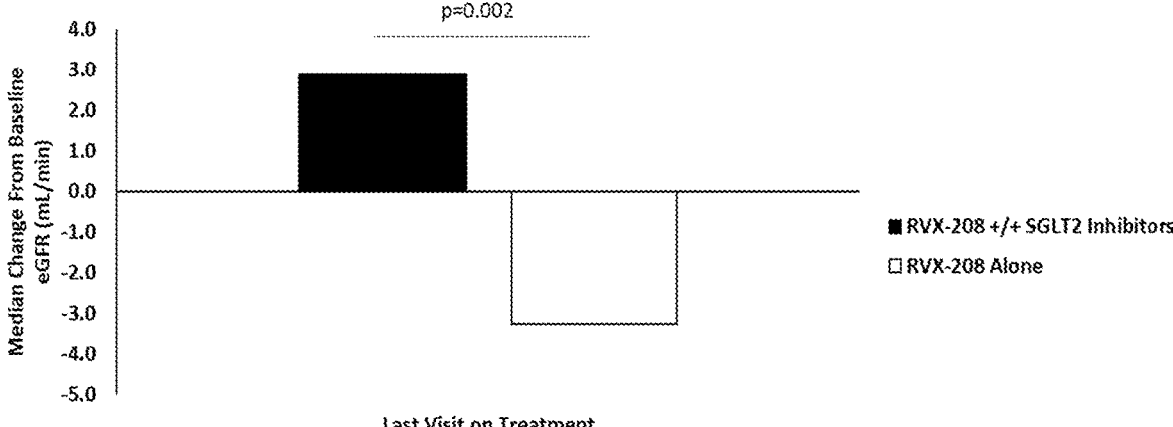
FIG. 2 depicts a comparison of the change of eGFR from baseline to LVT in patients administered RVX-208 with SGLT2 inhibitors versus patients administered RVX-208 without SGLT2 inhibitors.

FIGS. 1-2 each compare the median change of eGFR from baseline to last visit on treatment (LVT) between two groups of patients, a test group, and a control group, which are described as follows:

Patients treated with a SGLT2 inhibitor and RVX-208 (test) and patients treated with a SGLT2 inhibitor only and received a placebo (control) (FIG. 1); and, Patients treated with RVX-208 and a SGLT2 inhibitor (test) and patients treated RVX-208 only (control) (FIG. 2).

In FIG. 1, where the patients were treated with SGLT2 inhibitors and received either RVX-208 or a placebo, the effect of the co-administration of RVX-208 and SGLT2 inhibitors—quantified using change in eGFR levels from baseline—illustrated a significant increase in eGFR compared to placebo and SGLT2 inhibitors at LVT, with a median treatment difference of +7.4 mL/min/1.73 m$^2$ (p=0.05, Mann-Whitney), and mean treatment difference of +3.0 mL/min/1.73 m$^2$ (ANOVA 95% CI, −2.1 to 8.1) (p=0.24, ANOVA; p=0.05, Rank-ANOVA).

Figure 3:
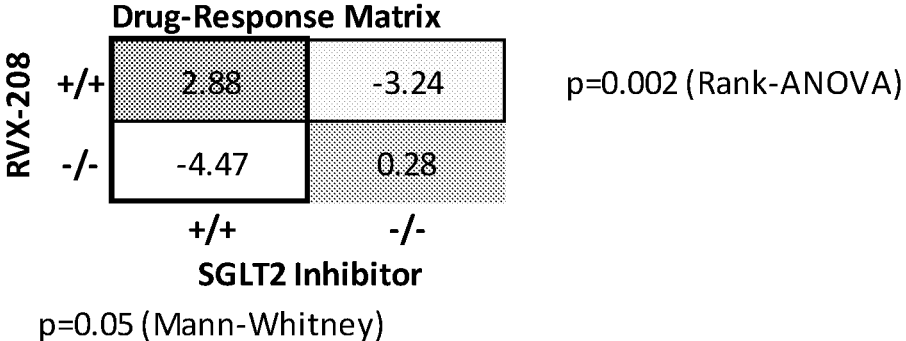
FIG. 3 depicts a drug interaction matrix, comparing the median change of eGFR from baseline to LVT in patients administered RVX-208 with or without SGLT2 inhibitors.
Figure 4:
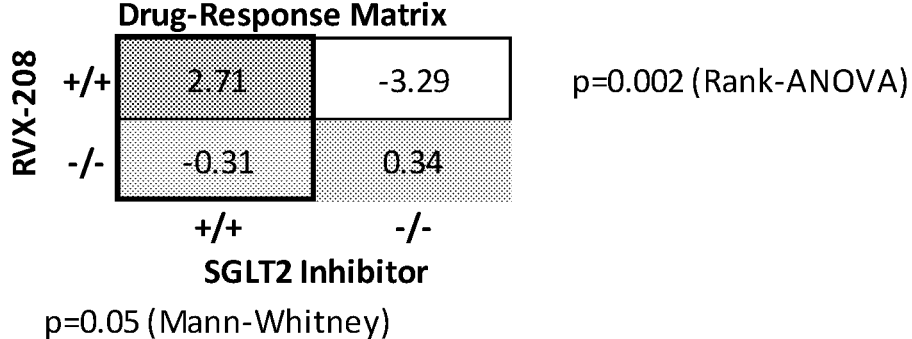
FIG. 4 depicts a drug interaction matrix, comparing the mean change of eGFR from baseline to LVT in patients administered RVX-208 with or without SGLT2 inhibitors.

Specifically, RVX-208 in combination with SGLT2 inhibitors the eGFR from a median of 114 mL/min at baseline to a median of 120 mL/min at last visit on treatment (LVT). The mean change from baseline to LVT in this combination therapy group was +2.7 mL/min/1.73 m$^2$ (FIG. 4); the median change from baseline to LVT was +2.9 mL/min/1.73 m$^2$ (FIG. 3). Comparatively, the SGLT2 inhibitor monotherapy group had a median eGFR of 109 mL/min at baseline and a median eGFR of 110 mL/min at LVT. The mean change from baseline to LVT in this group was −0.3 mL/min/1.73 m$^2$ (FIG. 4); the median change from baseline to LVT was −4.5 mL/min/1.73 m$^2$ (FIG. 3).

In FIG. 2, where patients were treated with the combination of RVX-208 and a SGLT2 inhibitor or with RVX-208 alone, the effect of the co-administration of RVX-208 and SGLT2 inhibitors—quantified using change in eGFR levels from baseline—illustrated a significant increase in eGFR compared to RVX-208 without SGLT2 inhibitors at LVT, with a median treatment difference of +6.1 mL/min/1.73 m$^2$ (p=0.0003, Mann-Whitney), and mean treatment difference of 6.0 mL/min/1.73 m$^2$ (ANOVA 95% CI, 2.3 to 9.7) (p=0.002, ANOVA; p=0.002, Rank-ANOVA).

Specifically, the RVX-208 monotherapy group had a median eGFR of 97 mL/min at baseline and a median eGFR of 96 mL/min at last visit on treatment (LVT). The mean change of eGFR from baseline to LVT in this group was −3.3 mL/min/1.73 m$^2$ (FIG. 4); the median change from baseline to LVT was −3.2 mL/min/1.73 m$^2$ (FIG. 3). The statistical parameters for the RVX-208 and SGLT2 inhibitor combination therapy are as described above.

In conclusion, the results depicted in FIGS. 1-4 indicate that RVX-208 monotherapy was not able to increase median or mean eGFR levels in patients with T2DM and a recent ACS. As for the SGLT2 monotherapy, although the monotherapy appeared to have a minor effect in increasing the median eGFR from baseline to LVT (i.e., 109 mL/min to 110 mL/min), the mean and median change values did not indicate any increase (i.e., −0.3 mL/min/1.73 m$^2$ and 4.5 mL/min/1.73 m$^2$ respectively). Thus, it was unexpected that a combination therapy of RVX-208 and SGLT2 inhibitor would result in increases that are of statistical significance in both median and mean HbA1c changes as well as median eGFR levels from baseline to LVT in the same patient population.

Change in eGFR Slope

The rate of change of eGFR (eGFR slope) from baseline to LVT in the patient population receiving the combination of an SGLT2 inhibitor in addition to RVX-208, the combination of an SGLT2 inhibitor in addition to placebo, and RVX-208 without an SGLT2 inhibitor was assessed from baseline to LVT. The eGFR slope for each patient was calculated using the difference between the eGFR measurements from baseline to LVT divided by the number of treatment days determined as the difference of the date of LVT and the baseline date +1.

Figure 5:
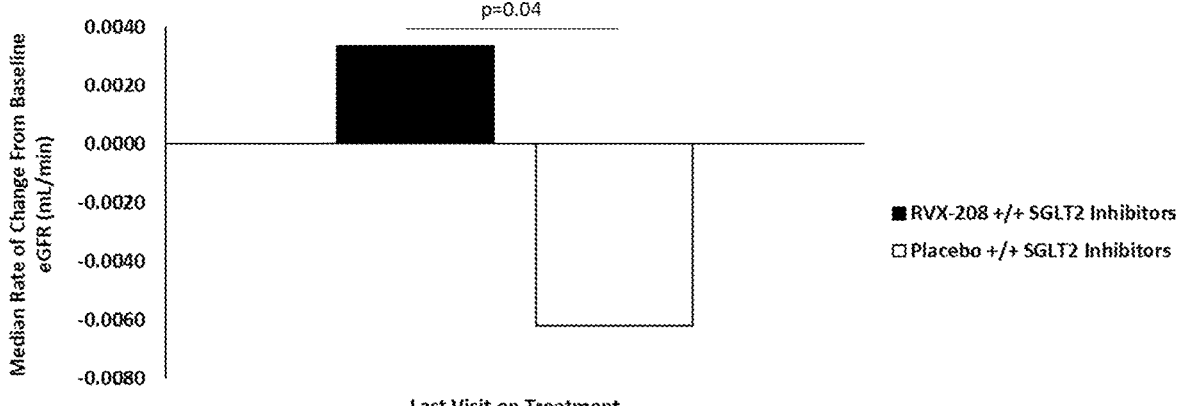
FIG. 5 depicts a comparison of the rate of change of eGFR (eGFR slope) from baseline to LVT in patients administered RVX-208 with SGLT2 inhibitors versus patients administered placebo with SGLT2 inhibitors.
Figure 6:
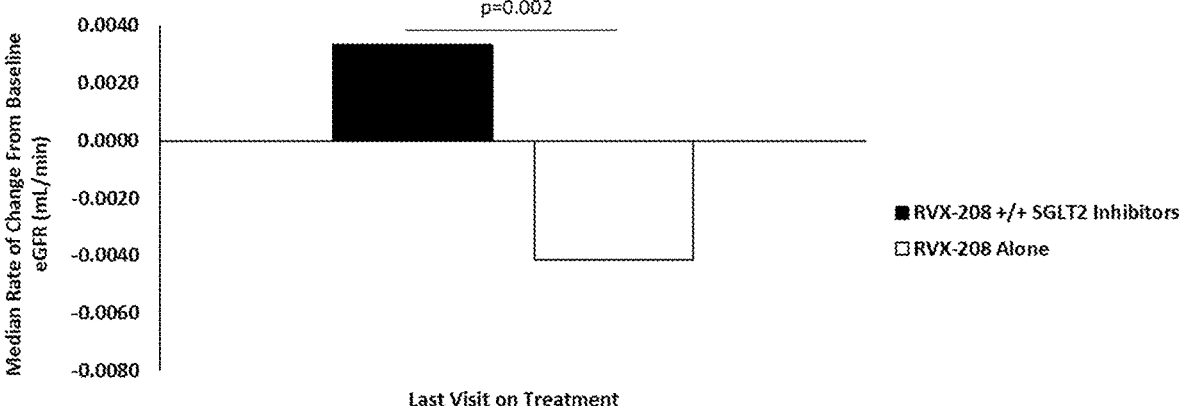
FIG. 6 depicts a comparison of the rate of change of eGFR (eGFR slope) from baseline to LVT in patients administered RVX-208 with SGLT2 inhibitors versus patients administered RVX-208 without SGLT2 inhibitors.

FIGS. 5-6 each compare the median rate of change in eGFR (eGFR slope) from baseline to last visit on treatment (LVT) between the same two groups of patients as described above for FIGS. 1-2.

In FIG. 5, where the patients were treated with SGLT2 inhibitors and received either RVX-208 or a placebo, the effect of the co-administration of RVX-208 and SGLT2 inhibitors—quantified using rate of change of eGFR from baseline—illustrated a significant improvement compared to placebo and SGLT2 inhibitors at LVT, with a median eGFR slope increase of 0.010 (p=0.04, Mann-Whitney) over a median of 748 days (2.05 years) of study drug exposure. Comparatively, the SGLT2 monotherapy was not able to increase the eGFR slope, with the median eGFR slope from baseline to LVT being −0.006 over a median of 734 days (2.01 years) of study drug exposure.

In FIG. 6, where patients were treated with the combination of RVX-208 and a SGLT2 inhibitor or with RVX-208 alone, the effect of the co-administration of RVX-208 and SGLT2 inhibitors—quantified using rate of change of eGFR from baseline—also illustrated a significant improvement compared to RVX-208 without SGLT2 inhibitors at LVT, with a median eGFR slope difference of 0.008 (p=0.002, Mann-Whitney). Comparatively, the RVX208 monotherapy was not able to increase the eGFR slope, with the median eGFR slope from baseline to LVT being −0.004 over a median of 785 days (2.15 years) of study drug exposure.

In conclusion, neither the RVX-208 monotherapy nor the SGLT2 monotherapy was able to increase the median eGFR slope in patients with T2DM and a recent ACS. Thus, it was unexpected that a combination therapy of RVX-208 and SGLT2 inhibitor would result in any increase in the median eGFR slope, let alone increases that are of statistical significance in the same patient population.

The invention claimed is:

1. A method for treating a kidney disease or an associated disorder as measured by an increase in estimated glomerular filtration rate (eGFR), the method comprising administering to a subject in need thereof a combination of a sodium-glucose transport protein 2 (SGLT2) inhibitor and 2-(4-(2-hydroxyethoxy)-3,5-dimethylphenyl)-5,7-dimethoxyqui-nazolin-4(3H)-one (RVX-208; RVX000222) or a pharmaceutically acceptable salt thereof, wherein the SGLT2 inhibitor is selected from empagliflozin, canagli-flozin, and dapagliflozin.

2. The method according to claim 1, comprising admin-istering to the subject a daily dose of 100-300 mg of 2-(4-(2-hydroxyethoxy)-3,5-dimethylphenyl)-5,7-dime-thoxyquinazolin-4(3H)-one (RVX-208; RVX000222) or an equivalent amount of a pharmaceutically acceptable salt thereof.

3. The method according to claim 2, comprising admin-istering to the subject, a daily dose of 200 mg of 2-(4-(2-hydroxyethoxy)-3,5-dimethylphenyl)-5,7-dimethoxyqui-nazolin-4(3H)-one (RVX-208; RVX000222) or an equivalent amount of a pharmaceutically acceptable salt thereof.

4. The method according to claim 1, wherein the 2-(4-(2-hydroxyethoxy)-3,5-dimethylphenyl)-5,7-dimethoxyqui-nazolin-4(3H)-one (RVX-208; RVX000222) or pharmaceu-tically acceptable salt thereof is administered simultaneously with the SGLT2 inhibitor in separate com-positions.

5. The method according to claim 1, wherein the 2-(4-(2-hydroxyethoxy)-3,5-dimethylphenyl)-5.7-dimethoxyqui-nazolin-4(3H)-one (RVX-208; RVX000222) or a pharma-ceutically acceptable salt thereof is administered with the SGLT2 inhibitor in a single composition.

6. The method according to claim 1, wherein the subject is a human.

7. The method according to claim 1, wherein the subject is a human with type 2 diabetes or chronic kidney disease.

8. The method according to claim 6, wherein the subject is a human on statin therapy.

9. The method according to claim 6, wherein the subject is a human with low HDL cholesterol (below 40 mg/dL for males and below 45 mg/dl for females) and a recent acute coronary syndrome (ACS) (preceding 7-90 days).

10. The method according to claim 1, wherein the kidney disease or an associated disorder is a kidney disease asso-ciated with reduced eGFR.

11. The method according to claim 10, wherein the kidney disease associated with reduced eGFR is also associated with type 2 diabetes or a diabetes-related disease or disorder.

12. The method according to claim 10, wherein the kidney disease associated with reduced eGFR is nephropathy.

13. The method according to claim 10, wherein the kidney disease associated with reduced eGFR is diabetic nephropa-thy.

14. The method according to claim 10, wherein the kidney disease associated with reduced eGFR is chronic kidney disease.

15. The method according to claim 10, wherein the chronic kidney disease is a comorbidity of type 2 diabetes.

16. The method according to claim 1, wherein the treating comprises improving renal function by increasing eGFR slope.

17. The method according to claim 1, wherein the treating comprises reducing the decline of renal function by increas-ing eGFR slope.

* * * * *